United States Patent [19]

König et al.

[11] 4,395,400
[45] Jul. 26, 1983

[54] NONAPEPTIDE, A PROCESS FOR ITS PREPARATION, AN AGENT CONTAINING IT AND ITS USE

[75] Inventors: Wolfgang König, Hofheim am Taunus; Rolf Geiger, Frankfurt am Main; Jürgen K. Sandow, Königstein, all of Fed. Rep. of Germany

[73] Assignee: Hoechst Aktiengesellschaft, Frankfurt am Main, Fed. Rep. of Germany

[21] Appl. No.: 268,677

[22] Filed: Jun. 1, 1981

[30] Foreign Application Priority Data

Jun. 3, 1980 [DE] Fed. Rep. of Germany ....... 3020941

[51] Int. Cl.$^3$ ..................... A61K 37/00; C07C 103/52
[52] U.S. Cl. ........................... 424/177; 260/112.5 LH
[58] Field of Search ............... 260/112.5 LH; 424/177

[56] References Cited

U.S. PATENT DOCUMENTS

| | | | |
|---|---|---|---|
| 3,853,834 | 12/1974 | Shields | 260/112.5 LH |
| 3,853,837 | 12/1974 | Fujino et al. | 260/112.5 LH |
| 3,855,198 | 12/1974 | Sarantakis | 260/112.5 LH |
| 3,856,769 | 12/1974 | Sakakibora et al. | 260/112.5 LH |
| 3,888,838 | 6/1975 | Immer et al. | 260/112.5 LH |
| 3,992,365 | 11/1976 | Beddell et al. | 260/112.5 LH |
| 4,003,884 | 1/1977 | Konig et al. | 260/112.5 LH |
| 4,024,248 | 5/1977 | Konig et al. | 260/112.5 LH |
| 4,118,483 | 10/1978 | Konig et al. | 260/112.5 LH |
| 4,275,001 | 6/1981 | Konig et al. | 260/112.5 LH |
| 4,301,066 | 11/1981 | Bellini et al. | 260/112.5 LH |

FOREIGN PATENT DOCUMENTS

| | | | |
|---|---|---|---|
| 2446005 | 4/1975 | Fed. Rep. of Germany | 260/112.5 |
| 2438350 | 2/1976 | Fed. Rep. of Germany | 260/112.5 |
| 135078 | 11/1979 | German Democratic Rep. | 260/112.5 LH |
| 1434694 | 5/1976 | United Kingdom | 260/112.5 LH |

*Primary Examiner*—Delbert R. Phillips
*Attorney, Agent, or Firm*—Curtis, Morris & Safford

[57] ABSTRACT

What are disclosed are a nonapeptide of the formula

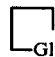

⌐
└Glu—His—Trp—Ser—Tyr—D-Aad(OBu$^t$)—

—Leu—Arg—Pro—NH—C$_2$H$_5$, wherein D-Aad (OBu$^t$) represents D-α-aminoadipic acid δ-tert. butyl ester, methods for making this peptide, pharmaceutical preparations containing this peptide, and methods for its use in increasing fertility or for contraception.

4 Claims, No Drawings

NONAPEPTIDE, A PROCESS FOR ITS PREPARATION, AN AGENT CONTAINING IT AND ITS USE

Gonadoliberin is a decapeptide of the following structure:

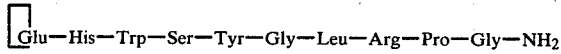

[Biochem. Biophys. Res. Commun. 43, 1334 (1971)]. It is formed in the hypothalamus and, in the pituitary, produces a stimulation of the luteotropic and follicle-stimulating hormones.

As is known, derivatives of these decapeptides having a stronger action are obtained if glycine is replaced in position 6 by certain D-aminoacids or if glycinamide in position 10 is replaced by ethylamine [J. Med. Chem. 16, 1144 (1973)]. Trifunctional D-aminoacids, the third function of which has been blocked by protective groups of the tert.-butyl type, prove particularly advantageous in position 6 (Peptides Chemistry, Structure, Biology, ed. R. Walter and J. Meienhofer, pp. 883–888, Ann Arbor, Mich. 1975). It has been found that O-tert.-butyl-D-serine has the strongest biological action. If, as in the case of D-tert.-butylleucine, the tert.-butyl group is very near to the peptide skeleton, the biological activity is very weak. If the tert.-butyl group is at a greater distance from the peptide chain, as in the case of the ω-tert.-butyl esters of D-Asp and D-Glu or in the case of ε-tert.-butoxycarbonyl-D-lysine, the biological action falls off in comparison with O-tert.-butyl-D-serine.

It has been found that a gonadoliberin-active peptide which has a particularly good activity is obtained if the glycine in position 6 of gonadoliberin is replaced by the D-α-aminoadipic acid δ-tert.-butyl ester, in which the tert.-butyl group is at a greater distance than in the case of the D-aspartic acid or D-glutamic acid compound, but is not at such a great distance as in the case of the D-lysine compound.

The invention relates to a peptide of the formula

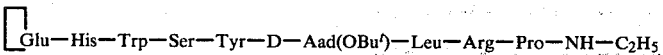

wherein D-Aad(OBu$^t$) represents D-α-aminoadipic acid δ-tert.-butyl ester.

The invention also relates to a process for the preparation of this peptide, which comprises:
(A) subjecting

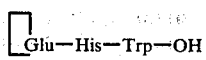

to a condensation reaction with H-Ser-Tyr-D-Aad-(OBu$^t$)-Leu-Arg-Pro-NH-C$_2$H$_5$,
(B) subjecting

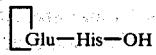

or Glu-His(Dnp)-OH to a condensation reaction with H-Trp-Ser-Tyr-D-Aad(OBu$^t$)-Leu-Arg-Pro-NH-C$_2$H$_5$, or
(C) subjecting

to a condensation reaction with H-His-Trp-Ser-Tyr-D-Aad(OBu$^t$)-Leu-Arg-Pro-NH-C$_2$H$_5$,
and, if appropriate, splitting off the Dnp protective groups.

The invention also relates to an agent containing the said decapeptide and to its use for increasing fertility or for contraception.

The azide method can be used particularly advantageously for the condensation reaction according to procedure A, since the precursor,

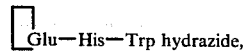

is a substance which can be prepared easily. The condensation reaction of

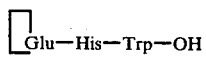

with the C-terminal hexapeptide can also be carried out by means of dicyclohexylcarbodiimide in conjunction with additives which decrease racemization, such as 1-hydroxybenzotriazole, N-hydroxysuccinimide or 3-hydroxy-4-oxo-3,4-dihydro-1,2,3-benzotriazine.

In procedure B, the methods described under A can be used to attach

to the C-terminal heptapeptide. The synthesis proceeds in an improved manner if the imidazole function of the histidine is intermediately protected with a 2,4-dinitrophenyl radical and if dicyclohexylcarbodiimide in conjunction with 3-hydroxy-4-oxo-3,4-dihydro-1,2,3-benzotriazine is used for the condensation reaction. In this method, the racemization of the histidine is less than 1–2%. After the coupling reaction, the 2,4-dinitrophenyl protective group is split off again by adding hydrazine to the reaction mixture.

In procedure C, the preferred reaction which is recommended is the use of an active ester of pyroglutamic acid for effecting the attachment, and the reaction can be catalyzed by adding 1-hydroxybenzotriazole. In particular, active esters of the phenyl type, such as 2,4,5-trichlorophenyl esters or 4-nitrophenyl esters, are suitable for this purpose. However, the reaction of pyroglutamic acid with the C-terminal octapeptide can also be carried out by means of the azide method, the DCCI method, the mixed anhydride method or other methods which are customary in peptide chemistry.

The synthesis of the particular C-terminal peptides can be effected, for example, in the manner shown in the three condensation reaction diagrams below.

Condensation reaction diagram A

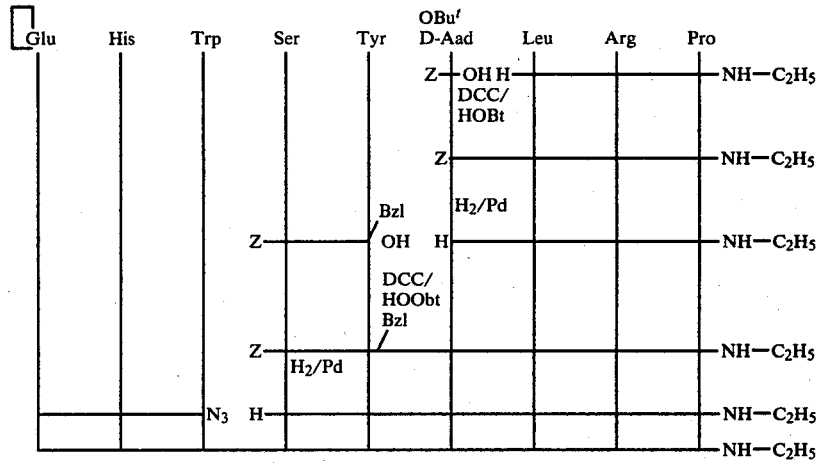

Condensation reaction diagram B

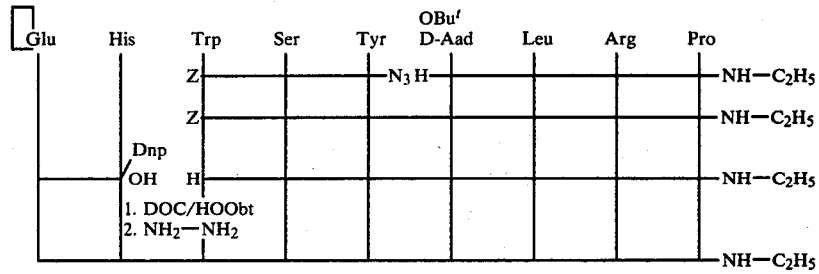

Condensation reaction diagram C

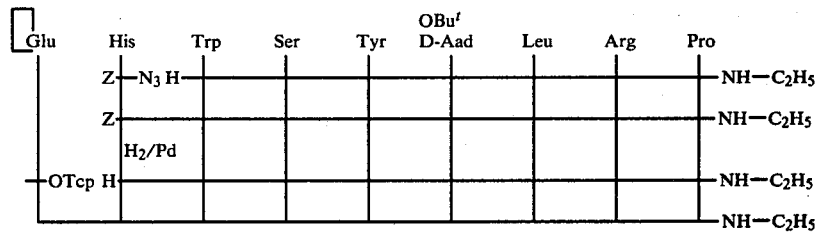

D-Aminoadipic acid occurs in nature. A preferred source is cephalosporin C, in which it forms the side chain. It can be obtained easily in large quantities by a suitable working-up process in the isolation of 7-aminocephalosporanic acid. As opposed to this, the chemical synthesis of D-aminoadipic acid is more involved, particularly because of a wasteful resolution of a racemate. In addition to the good biological action of the compound, the ready accessibility of naturally occurring D-aminoadipic acid constitutes a further advantage of the invention. Z-D-Aad-OBzl, which has already been described in the literature [Bull. Soc. Chem. Belge 77, 587–596 (1968)] can be reacted with isobutylene in methylene chloride with $H_2SO_4$ as a catalyst to give the corresponding δ-tert.-butyl ester. Alkaline saponification gives Z-D-Aad(OBu$^t$)-OH, which can be used for the synthesis in accordance with condensation reaction diagram A.

The nonapeptide according to the invention is distinguished by good solubility in aqueous buffer solutions. This makes the compound suitable for intranasal administration, for which, as shown by experience, solubility can be the limiting factor. Its solubility is appreciably greater than that of other gonadoliberin analogs having a comparable degree of effectiveness, particularly the D-Trp[6] or D-His(Bzl)[6] analogs.

At a low dosage, the nonapeptide has a fertility-increasing action as a result of the secretion of gonadotropic hormones, and, at a high dosage, repeated daily, has an inhibitory effect on the secretion of gonadotropic hormones and thus has a contraceptive action.

The preferred method of administration in humans is intranasal administration, since absorption of the compound from the gastro-intestinal tract is only slight and parenteral administration is inappropriate for the patient. About 0.1 ml of a buffer solution, in which the necessary quantity of the active compound is dissolved, is sprayed into the nose via a spray jet, by means of a dosing atomizer.

Examples of indications are, in women, primary amenorrhea, but chiefly secondary amenorrhea, and corpus luteum insufficiency and, in the case of men, oligospermia. It is also possible to treat delayed puberty in both sexes and cryptorchidism in boys.

In general, the daily dose for intranasal administration varies between 0.025 and 0.1 mg/patient, but in most cases it is only necessary to administer the substance every 2 to 3 days because of its long-term action. In cryptorchidism, doses as low as 0.01 to 0.025 mg per day and per patient are sufficient.

For contraceptive use, the nonapeptide must be administered intranasally at a dosage of 0.1–0.4 mg per day, preferably 0.1 mg in the morning and at night. If administered parenterally, the dosages can be reduced by about a power of ten compared with the intranasal dose.

In veterinary medicine, it is preferable to administer the nonapeptide parenterally. It can be used for the treatment of acyclic animals and for inducing and synchronizing ovulation. The dose varies, depending on the species of animal. Recommended doses are, for example, 0.01–0.02 mg in the case of cattle, 0.02–0.04 mg in the case of mares and 0.0005–0.0008 mg in the case of rabbits.

EXAMPLE 1

(a) Z-D-Aad(OBu$^t$)-OBzl 400 ml of isobutylene are added to a solution of 40 g (approx. 104 mmoles) of Z-D-Aad-OBzl in 400 ml of methylene chloride, followed, at $-20°$, by 4 ml of concentrated sulfuric acid. The mixture is allowed to stand in an autoclave for 3 days at room temperature. The batch is stirred with NaHCO$_3$ solution in order to neutralize the sulfuric acid and the excess isobutylene is removed by means of a stream of nitrogen. The methylene chloride phase is extracted by shaking with water and is dried over Na$_2$SO$_4$ and concentrated. This leaves 46.3 g of an oil, which is chromatographed on 500 g of silica gel using a 9:1 mixture of methylene chloride and acetone. The eluate, which contains Z-Aad-(OBu$^t$)-OBzl, is concentrated. Yield: 42.35 g of a pale oil (92%).

(b) Z-D-Aad(OBu$^t$)-OH.cyclohexylamine 40 ml of water and 87.4 ml of 1 N NaOH are added to a solution of 36.7 g (83.1 mmoles) of Z-D-Aad(OBu$^t$)-OBzl in 175 ml of dioxane. The mixture is stirred for 3 hours at room temperature, neutralized with a little KHSO$_4$ solution and concentrated in vacuo. The residue is partitioned between 300 ml of ethyl acetate and 87 ml of 1 N sulfuric acid, while cooling with ice. The ethyl acetate phase is extracted by shaking once with a solution of KHSO$_4$ and twice with water and is dried over Na$_2$SO$_4$ and concentrated. The oil which remains is dissolved in ether. 9.45 ml of cyclohexylamine are added to this solution and the mixture is allowed to stand for 4 hours in a cooling chamber. The precipitate is filtered off, washed with ether and dried. Yield: 30.1 g (80%), melting point 135°, $[\alpha]_D^{23} = -7.1°$ (c=1, in methanol).

C$_{24}$H$_{38}$N$_2$O$_6$ (450.59) calculated: C 63.97; H 8.50; N 6.22; found: 63.6; 8.5; 6.3

(c) Z-D-Aad(OBu$^t$)-Leu-Arg-Pro-NH-C$_2$H$_5$, C$_{37}$H$_{60}$N$_8$O$_8$ (MW 744.95)

9 g (20 mmoles) of Z-D-Aad(OBu$^t$)-OH.cyclohexylamine are partitioned between 40 ml of ethyl acetate and 20 ml of 1 N H$_2$SO$_4$. The ethyl acetate phase is extracted by shaking successively with 10 ml of KHSO$_4$/K$_2$SO$_4$ solution and with 30 ml of water and is dried over Na$_2$SO$_4$ and concentrated. The oily residue is dissolved in 50 ml of dimethylformamide together with 15.11 g (20 mmoles) of H-Leu-Arg-Pro-NH-C$_2$H$_5$ ditosylate and 2.7 g (20 mmoles) of 1-hydroxybenzotriazole (=HOBt). The solution is cooled to 0° C. and 5.12 ml (40 mmoles) of N-ethylmorpholine and 4.53 g (22 mmoles) of dicyclohexylcarbodiimide are added. The mixture is stirred for one hour at 0° C. and for 6 hours at room temperature and is left to stand overnight at room temperature, the precipitate which has been deposited is filtered off and the filtrate is partitioned between 250 ml of n-butanol and 250 ml of saturated NaCl solution. The n-butanol phase is extracted by shaking with twice 125 ml of saturated NaHCO$_3$ solution and with 125 ml of water. The n-butanol phase is concentrated and the residue is triturated with 200 ml of ethyl acetate. 200 ml of petroleum ether are also added to the mixture and the precipitate is filtered off. Yield 15.05 g. The crude substance is recrystallized from 110 ml of ethyl acetate. The yield is then 10.71 g (72%). The substance is amorphous and begins to decompose above 70° C. $[\alpha]_D^{22} = -41.4°$ (c=1, in methanol). A further 2.88 g of substance can be precipitated from the mother liquor by adding petroleum ether. Total yield 13.59 g (91%).

(d) H-D-Aad(OBu$^t$)-Leu-Arg-Pro-NH-C$_2$H$_5$.2HCl, C$_{29}$H$_{56}$Cl$_2$N$_8$O$_6$ (MW 683.7)

12.5 g (approx. 16.8 mmoles) of Z-D-Aad(OBu$^t$)-Leu-Arg-Pro-NH-C$_2$H$_5$ are dissolved in 150 ml of methanol and subjected to catalytic hydrogenation at pH 4.5 with the addition of a Pd/BaSO$_4$ catalyst and while feeding in 2 N methanolic hydrochloric acid (by means of an autotitrator). When hydrogenation is complete, the catalyst is filtered off and the filtrate is concentrated. The residue is triturated with ethyl acetate and the product is filtered off and dried. Yield: 10.85 g (94%) of amorphous substance. Melting point 82°–85°, $[\alpha]_D^{23} = -48.9°$ (c=1, in 90 percent strength acetic acid).

(e) Z-Trp-Ser-Tyr-D-Aad(OBu$^t$)-Leu-Arg-Pro-NH-C$_2$H$_5$, C$_{60}$H$_{48}$N$_{12}$O$_{13}$, (MW 1181.4)

4.51 g (7.7 mmoles) of Z-Trp-Ser-Tyr hydrazide are dissolved in 40 ml of a 1:1 mixture of dimethylformamide and dimethylacetamide. 4.31 ml of 7 N HCl (about 30 mmoles) in dioxane and 1.08 ml (9.1 mmoles) of tert.-butyl nitrite are added to the mixture at $-30°$ C. The mixture is stirred for 20 minutes at $-10°$ C., 320 mg (4.7 mmoles) of NaN$_3$ are added, stirring is continued for a further 5 minutes at $-10°$ C., the mixture is cooled to $-40°$ C., 5.85 ml (45 mmoles) of N-ethylmorpholine and 5.13 g (7.5 mmoles) of H-D-Aad(OBu$^t$)-Leu-Arg-Pro-NHC$_2$H$_5$.2HCl are added and stirring is continued for 6 hours at 0° C. The mixture is then allowed to stand for two days at 4° C. A precipitate which is formed is filtered off. The filtrate is partitioned between 200 ml of saturated NaCl solution and 150 ml of n-butanol. The n-butanol phase is extracted by shaking with two 75 ml portions of KHSO$_4$ solution and with 75 ml of saturated NaHCO$_3$ solution and is concentrated. The residue is triturated with 100 ml of ethyl acetate and the product is filtered off and dried. Yield: 7.9 g (89%) of amorphous substance. $[\alpha]_D^{22} = -27.8°$ (c=1, in 90 percent strength acetic acid), decomposes above 138° C.

(f)
H-Trp-Ser-Tyr-D-Aad(OBu$^t$)-Leu-Arg-Pro-NH-C$_2$H$_5$.2HCl, C$_{52}$H$_{80}$Cl$_2$N$_{12}$O$_{11}$ (MW 1120.22)

7.7 g (about 6.5 mmoles) of Z-Trp-Ser-Tyr-D-Aad-(OBu$^t$)-Leu-Arg-Pro-NH-C$_2$H$_5$ are subjected to catalytic hydrogenation analogously to Example 1d. Yield: 6.27 g (86%) of amorphous substance. $[\alpha]_D^{22} = -22.2°$ (c=1, in 90 percent strength acetic acid).

(g)

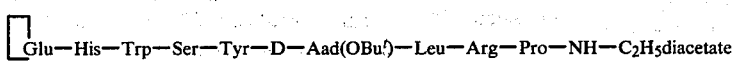Glu—His—Trp—Ser—Tyr—D—Aad(OBu$^t$)—Leu—Arg—Pro—NH—C$_2$H$_5$diacetate 0.325 ml of N-ethylmorpholine and 550 mg of dicyclohexylcarbodiimide are added at 0° C. to a solution of 1.1 g (2.5 mmoles) of

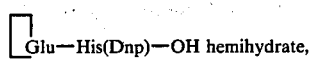Glu—His(Dnp)—OH hemihydrate, 2.8 g (2.5 mmoles) of H-Trp-Ser-Tyr-D-Aad(OBu$^t$)-Leu-Arg-Pro-NH-C$_2$H$_5$.2HCl and 407 mg of 3-hydroxy-4-oxo-3,4-dihydro-1,2,3-benzotriazine in 15 ml of dimethylacetamide. The mixture is stirred for 2-3 hours at 0° C. and is left to stand overnight at room temperature. The precipitate is filtered off. It is rinsed with 5 ml of dimethylacetamide. 0.25 ml of 100 percent strength hydrazine hydrate is added to the filtrate and the mixture is allowed to stand for 4 hours at room temperature. The substance is then precipitated by means of 140 ml of ethyl acetate and is filtered off. The precipitate is triturated in about 10 ml of methanol and is again precipitated by means of 140 ml of ethyl acetate. The precipitate is partitioned between 100 ml of n-butanol and 100 ml of saturated aqueous NaHCO$_3$ solution. The n-butanol phase is extracted by shaking with 70 ml of NaHCO$_3$ solution and is concentrated. The residue is dissolved in approx. 30–40 ml of dilute acetic acid and is chromatographed, in the form of the acetate, on a strongly basic ion exchanger. The eluate is concentrated and chromatographed on a hydroxypropylated, crosslinked dextran gel using a water/acetic acid/n-butanol mixture (10:0.8:1 parts by volume). Yield 1.16 g (33%). $[\alpha]_D^{21} = -41.6°$ (c=1, in methanol). Aminoacid analysis indicates that the aminoacid composition is correct and that the protein content is 85–90%. The UV spectrum shows the characteristic spectrum of tryptophan and indicates a protein content of 87%.

EXAMPLE 2

(a)
Z-His-Trp-Ser-Tyr-D-Aad(OBu$^t$)-Leu-Arg-Pro-NH-C$_2$H$_5$ 207 mg (3 mmoles) of NaNO$_2$, dissolved in a little water, are added at 0° C. to a solution of 910 mg (3 mmoles) of Z-His hydrazide in 12 ml of 1 N HCl. After the mixture has been at 0° C. for 5 minutes, 20 ml of cold ethyl acetate are added and the pH is adjusted to 9 with cold saturated sodium carbonate solution. The ethyl acetate phase is separated off, the aqueous phase is extracted again with ethyl acetate and the combined ethyl acetate phases are dried over Na$_2$SO$_4$ and concentrated to about 2 ml. A solution of 1.12 g (1 mmole) of H-Trp-Ser-Tyr-D-Aad(OBu$^t$)-Leu-Arg-Pro-NH-C$_2$H$_5$.2HCl in approx. 3 ml of dimethylformamide and 0.39 ml (3 mmoles) of N-ethylmorpholine are added to the concentrate. On the following day, the mixture is partitioned between 50 ml of n-butanol and 50 ml of saturated NaHCO$_3$ solution. The n-butanol phase is extracted by shaking with two 25 ml portions of saturated NaHCO$_3$ solution and with 25 ml of water and is concentrated. The residue is triturated with ether and the product is filtered off and dried. Yield: 1.3 g (100%), melting point 133°–135°, with decomposition. $[\alpha]_D^{22} = -37.9°$ (c=1, methanol).

(b)
H-His-Trp-Ser-D-Aad(OBu$^t$)-Leu-Arg-Pro-NH-C$_2$H$_5$.2HCl 1.3 g of Z-His-Trp-Ser-Tyr-D-Aad(OBu$^t$)-Leu-Arg-Pro-NH-C$_2$H$_5$ are dissolved in methanol and subjected to catalytic hydrogenation (Pd/BaSO$_4$ catalyst) at pH 4.5, 2 N methanolic hydrochloric acid being added (by means of an autotitrator). When the reaction is complete, the catalyst is filtered off and the filtrate is concentrated. The residue is triturated with ether and the product is filtered off and dried. Yield 920 mg (73%), melting point 146–149, with decomposition. $[\alpha]_D^{21} = -31.9°$ (c=1, methanol).

(c)

Glu—His—Trp—Ser—Tyr—D—Aad(OBu$^t$)—Leu—Arg—Pro—NH—C$_2$H$_5$.acetate 0.125 ml of N-ethylmorpholine and 155 mg of [Glu-OTcp are added to a solution of 628 mg (0.5 mmole) of H-His-Trp-Ser-Tyr-D-Aad(OBu$^t$)-Leu-Arg-Pro-NH-C$_2$H$_5$.2HCl and 67.5 mg of 1-hydroxybenzotriazole in 1 ml of dimethylformamide. The mixture is left to stand for one day at room temperature, 0.1 ml of hydrazine hydrate is added and the mixture is stirred for 2 hours at room temperature and partitioned between 10 ml of n-butanol and 10 ml of saturated NaHCO$_3$ solution. The n-butanol phase is concentrated and the residue is triturated with ether and the product is filtered off and dried. The crude substance thus obtained is dissolved in dilute acetic acid and is chromatographed analogously to Example 1g on a strongly basic ion exchanger and on a hydroxypropylated, crosslinked dextran gel. Yield 180 mg (25%); thin layer chromatogram: corresponds to the material obtained in Example 1g (on silica gel G using chloroform/methanol/glacial acetic acid/water (60:45:6:14 parts by volume)).

EXAMPLE 3

(a)
Z-Ser-Tyr(Bzl)-D-Aad(OBu$^t$)-Leu-Arg-Pro-NH-C$_2$H$_5$ 0.26 ml of N-ethylmorpholine and 440 mg of dicyclohexylcarbodiimide are added at 0° C. to a solution of 1 g (approx. 2 mmoles) of Z-Ser-Tyr(Bzl)-OH, 1.4 g (2 mmoles) of H-D-Aad(OBu$^t$)-Leu-Arg-Pro-NH-C$_2$H$_5$.2HCl and 0.326 g (2 mmoles) of 3-hydroxy-4-oxo-3,4-dihydro-1,2,3-benzotriazine in 8 ml of dimethylacetamide. The mixture is stirred for two hours at 0° C. and is then left to stand overnight at room temperature. The precipitate is filtered off and the filtrate is partitioned between 50 ml of n-butanol and 50 ml of saturated NaCl solution. The n-butanol phase is extracted by shaking with two 25 ml portions of saturated NaHCO$_3$ solution and with 25 ml of water and is concentrated. The residue is triturated with ether and the product is filtered off and dried. Yield 2.05 g (94%), amorphous. $[\alpha]_D^{22} = -37.4°$ (c=1, methanol).

(b) H-Ser-Tyr-D-Aad(OBu$^t$)-Leu-Arg-Pro-NH-C$_2$H$_5$.2HCl 1.9 g (1.75 mmoles) of Z-Ser-Tyr(Bzl)-D-Aad(OBu$^t$)-Leu-Arg-Pro-NH-C$_2$H$_5$ are dissolved in 150 ml of methanol and subjected to catalytic hydrogenation analogously to Example 1d. The residue is triturated with ether and the product is filtered off and dried. Yield 1.33 g (83%), melting point 134°–136°. $[\alpha]_D^{22} = -38.4°$ (c=1, methanol).

(c)

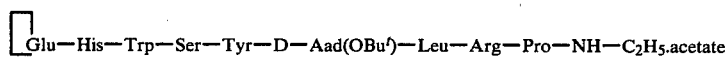
⌐Glu—His—Trp—Ser—Tyr—D—Aad(OBu$^t$)—Leu—Arg—Pro—NH—C$_2$H$_5$.acetate 0.66 ml of a 6.05 N HCl/dioxane solution and 1.2 ml of a 10 percent strength solution of tert.-butyl nitrite in absolute dioxane are added at −30° C. to a solution of 500 mg of

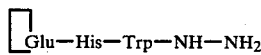
⌐Glu—His—Trp—NH—NH$_2$ in 6 ml of dimethylformamide. The mixture is stirred for 20 minutes at −10° C. and 918 mg of crude H-Ser-Tyr-D-Aad(Bu$^t$)-Leu-Arg-Pro-NH-C$_2$H$_5$.2HCl and 0.78 ml of N-ethylmorpholine are added at −40° C. The mixture is left to stand overnight at 4° C. and is concentrated and the residue is triturated with ether. The substance is dissolved in water and is chromatographed, analogously to Example 1g, on a strongly basic ion exchanger and then on a hydroxypropylated, cross-linked dextran gel. Yield 410 mg (31%); thin layer chromatogram: identical with the substance obtained in Example 1g.

We claim:

1. The peptide of the formula

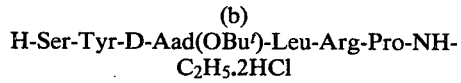
⌐Glu—His—Trp—Ser—Tyr—D-Aad(OBu$^t$)—

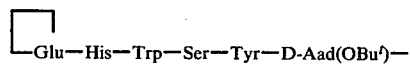
—Leu—Arg—Pro—NH—C$_2$H$_5$ in which -D-Aad(OBu$^t$)- represents D-α-aminoadipic acid δ-tert.-butyl ester.

2. A pharmaceutical composition for increasing fertility or for inducing contraception, said composition comprising an amount, pharmaceutically effective for the intended use of the preparation, of the peptide of claim 1 dissolved in an aqueous buffer solution as a carrier.

3. A method for increasing fertility in a patient requiring such treatment which comprises intranasally administering to said patient a low dose of the peptide of claim 1.

4. A method for inducing contraception in a patient requiring such treatment which comprises nasally administering to said patient a high dose of the peptide of claim 1 on a repeated daily basis.

* * * * *